United States Patent [19]

Tomcufcik et al.

[11] Patent Number: 4,562,189

[45] Date of Patent: Dec. 31, 1985

[54] PYRAZOLYLPIPERAZINES

[75] Inventors: Andrew S. Tomcufcik, Old Tappan, N.J.; Walter E. Meyer, Suffern, N.Y.; Shin S. Tseng, Bridgewater, N.J.

[73] Assignee: American Cyanamid Company, Stamford, Conn.

[21] Appl. No.: 659,116

[22] Filed: Oct. 9, 1984

[51] Int. Cl.$^4$ ................ A61K 31/415; A61K 31/495; C07D 295/00; C07D 231/38

[52] U.S. Cl. .................................. 514/252; 544/360; 544/366; 544/371

[58] Field of Search ...................... 544/360, 366, 371; 424/250; 514/407, 252; 548/374, 375

[56] References Cited

U.S. PATENT DOCUMENTS

| | | | |
|---|---|---|---|
| 3,534,058 | 10/1970 | Santilli | 548/375 |
| 3,839,336 | 10/1974 | Borck et al. | 544/371 |
| 3,920,693 | 11/1975 | Ege | 548/375 |
| 3,926,999 | 12/1975 | Poetsch | 544/379 |
| 3,944,551 | 3/1976 | Regnier et al. | 544/363 |
| 3,988,348 | 10/1976 | Cross et al. | 548/375 |
| 4,421,753 | 12/1983 | Tomcufcik et al. | 544/366 |

FOREIGN PATENT DOCUMENTS 2261351  6/1974  Fed. Rep. of Germany ...... 544/371

Primary Examiner—Donald G. Daus
Assistant Examiner—Stephen M. Kapner
Attorney, Agent, or Firm—Edward A. Conroy, Jr.

[57] ABSTRACT

This disclosure describes novel pyrazolylpiperazines useful as hypotensive agents in mammals and as intermediates for the preparation of certain pyrazolo[1,5-a]pryrimidines.

19 Claims, No Drawings

PYRAZOLYLPIPERAZINES

BRIEF SUMMARY OF THE INVENTION

This invention relates to new organic compounds and, more particularly, is concerned with novel pyrazolylpiperazines which have hypotensive activity. The compounds of the present invention may be represented by the following structural formula:

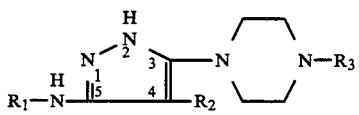

wherein $R_1$ is hydrogen, alkyl($C_1$–$C_3$)carbonyl or alkyl($C_1$–$C_3$)sulfonyl; $R_2$ is cyano or carbamoyl; and $R_3$ is methyl, benzyl, 3-phenylpropyl, 3-phenyl-2-propenyl, β-hydroxyethyl, 3-chlorobenzyl, 4-chlorobenzyl, 3,4,-dichlorobenzyl, 2,6-dichlorobenzyl, 2-phenoxyethyl, 3-phenoxypropyl, 4-phenoxybutyl, 3-methoxybenzyl, 4-methoxybenzyl, 2-furanylmethyl, 2-pyridyl or [(2-phenyl-2H-1,2,3-triazol-4-yl)methyl] and the pharmacologically acceptable acid-addition salts thereof.

The invention also includes novel compositions of matter containing of the above-defined compounds which are useful as hypotensive agents and the method for treating hypertension in mammals therewith.

DETAILED DESCRIPTION OF THE INVENTION

The novel compounds of the present invention are in general obtainable as colorless, white, off-white, or cream colored crystalline solids having characteristic melting points and absorption spectra. They are appreciably soluble in many organic solvents such as lower alkanols, chloroform, tetrahydrofuran, acetonitrile, ethyl acetate and the like but are generally only slightly soluble in water. These compounds are organic bases and thus are capable of forming acid-addition salts with a variety of organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic and related acids. The acid-addition salts of the novel compounds of the present invention are, in general crystalline solids relatively soluble in water, methanol and ethanol but relatively insoluble in non-polar organic solvents such as diethyl ether, benzene, toluene and the like. For purposes of this invention the free bases are equivalent to their non-toxic acid-addition salts.

The novel pyrazolylpiperazine compounds of the present invention where $R_1$ is hydrogen and $R_2$ is cyano in structural formula I may be readily prepared as set forth in the following reaction scheme.

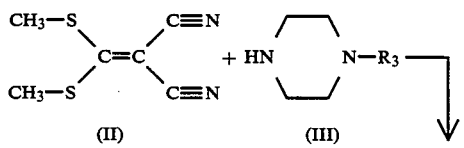

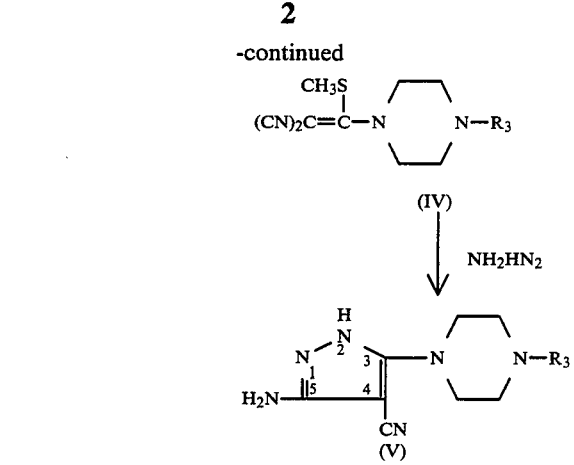

wherein $R_3$ is as hereinabove described.

In accordance with the above reaction sequence, [bis(methylthio)methylene]propanedinitrile II and a piperazine compound III where $R_3$ is as hereinabove described are refluxed in acetonitrile, ethanol or a similar solvent for 2–20 hours, giving a solution of [(4-substituted-1-piperazinyl)(methylthio)methylene]propanedinitrile IV, which is then refluxed with hydrazine hydrate in the solvent for 1–18 hours to provide the desired pyrazolylpiperazine products (V) of the invention.

The above 4-pyrazolecarbonitrile products where $R_2$ is cyano in structural formula I may be readily converted to the 4-pyrazolecarboxamide products of the invention by heating the nitrile with concentrated sulfuric acid for 2–6 hours, allowing the mixture to stand, then cooling, making basic with ammonium hydroxide and collecting the product which may be purified by conventional means using ethanol and water.

The pyrazolylpiperazine products where $R_1$ is hydrogen and $R_2$ is cyano in structural formula I may be acylated at the $R_1$ position by stirring with an alkanoic acid anhydride at room temperature in an inert solvent for 18 hours.

Accordingly, the pyrazolylpiperazine products where $R_1$ is hydrogen and $R_2$ is cyano in structural formula I may be reacted with an alkyl($C_1$–$C_3$)sulfonyl chloride in a solvent such as pyridine for 16 hours. The reaction mixture is evaporated in vacuo and the residue in water is adjusted to pH 8.0 with saturated sodium bicarbonate to precipitate the product where $R_1$ is alkyl($C_1$–$C_3$)sulfonyl.

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y., having an average mean arterial blood pressure of 170±1.5 mm of mercury are used in the test. One to 3 rats are used per test compound. A rat is dosed by gavage with a test compound, suspended in 2% preboiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention which were obtained using one or two rats, at a dose of 100 mg/kg of body weight appear below in Table I.

TABLE I

Hypotensive Activity in Spontaneously Hypertensive Rats

| Compound | Mean Arterial Blood Pressure (mm of mercury) |
|---|---|
| 3-Amino-5-(4-benzyl-1-piperazinyl)-4-pyrazolecarbonitrile | 100 |
| | 99 |
| 3-Amino-5-(4-benzyl-1-piperazinyl)-4-pyrazolecarboxamide | 91 |
| | 104 |
| 3-Amino-5-[4-[(3,4,-dichlorophenyl)methyl]-1-piperazinyl]-1H—pyrazole-4-carbonitrile | 102 |
| | 111 |
| 3-Amino-5-[4-(3-phenylpropyl)-1-piperazinyl]-1H—pyrazole-4-carbonitrile, hydrochloride | 88 |
| | 99 |
| 3-Amino-5-]4-(2-furanylmethyl)-1-piperazinyl]-1H—pyrazole-4-carbonitrile | 113 |
| | 98 |
| 5-Amino-3-[-4-[(2-phenyl-2H—1,2,3-triazol-4-yl)-methyl]-1-piperazinyl]-1H—pyrazole-4-carbonitrile | 110 |
| | 112 |
| 5-Amino-3-[4-(3-phenoxypropyl)-1-piperazinyl]-1H—pyrazole-4-carbonitrile | 107 |
| | 82 |
| 5-Amino-3-[4-(4-phenoxybutyl)-1-piperazinyl]-1H—pyrazole-4-carbonitrile | 95 |
| | 97 |
| 5-Amino-4-[4-(2-phenoxyethyl)-1-piperazinyl]-1H—pyrazole-4-carbonitrile | 121 |
| | 106 |
| 3-Amino-5-[4-(3-phenyl-2-propenyl)-1-piperazinyl]-1H—pyrazole-4-carbonitrile | 102 |
| | 86 |
| N—[4-Cyano-5-[4-(phenylmethyl)-1-piperazinyl]-1H—pyrazol-3-yl]acetamide | 99 |
| | 83 |
| N—[4-Cyano-5-[4-(4-phenylmethyl)-1-piperazinyl]-1H—pyrazol-3-yl]methanesulfonamide | 120 |
| 3-Amino-5-(4-methyl-1-piperazinyl)-1H—pyrazole-4-carbonitrile | 95 |
| 3-Amino-5-[4-(2-pyridinyl)-1-piperazinyl]-1H—pyrazole-4-carbonitrile | 141 |
| 3-Amino-5-[4-(2-hydroxyethyl)-1-piperazinyl]-1H—pyrazole-4-carbonitrile | 125 |
| 3-Amino-5-[4-[3-chlorophenyl)methyl]-1-piperazinyl]-1H—pyrazole-4-carbonitrile | 95 |
| 3-Amino-5-[4-[(2,6-dichlorophenyl)methyl]-1-piperazinyl]-1H—pyrazole-4-carbonitrile | 125 |
| 3-Amino-5-[4-[(4-methoxyphenyl)methyl]-1-piperazinyl]-1H—pyrazole-4-carbonitrile | 99 |
| 3-Amino-5-[4-](3-methoxyphenyl)methyl]-1-piperazinyl]-1H—pyrazole-4-carbonitrile | 113 |
| 3-Amino-5-[4-[(4-chlorophenyl)methyl]-1-piperazinyl]-1H—pyrazole-4-carbonitrile | 84 |

The novel compounds of the present invention have been found to be highly useful for lowering elevated blood pressure in mammals when administered in amounts ranging from about 5 mg to about 100 mg per kilogram of body weight per day. A preferred dosage regimen for optimum results would be from about 5 mg to about 50 mg per kilogram of body weight per day, and such dosage units are employed that a total of from about 350 mg to about 3.5 g of the active compound for a subject of about 70 kg of body weight are administered in a 24 hour period.

The dosage regimens for lowering elevated blood pressure may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporaated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethyleneglycol), suitable mixtures thereof, and vegetable oils.

The invention will be described in greater detail in conjunction with the following specific examples.

EXAMPLE 1

1-(3,4-Dichlorobenzyl)piperazine

A mixture of 39.0 g (0.2 moles) of 3,4-dichlorobenzyl chloride, 31.6 g (0.2 moles) of ethyl N-piperazinocarboxylate, 22.0 g (0.21 moles) of anhydrous sodium carbonate and 200 ml of xylene was refluxed for 3 hours using a Dean-Stark trap. Then the mixture was stirred at room temperature for 16 hours, filtered and washed with xylene. The filtrate was evaporated in vacuo and gave a syrup. A 750 ml amount of 4N potassium hydroxide in 95% ethanol was added to the syrup and the mixture was refluxed for 18 hours. The reaction mixture was evaporated to a paste and 250 ml of water was added. The solution was extracted twice with 250 ml of chloroform. The extracts were combined, dried over magnesium sulfate and filtered. The filtrate was evaporated in vacuo and gave a syrup. The syrup was distilled, bp 132°–135° C./0.05 mm of mercury and gave 9.3 g of 1-(3,4-dichlorobenzyl)piperazine as a colorless liquid.

EXAMPLE 2

1-(4-Phenoxybutyl)piperazine

A mixture of 45.8 g (0.2 moles) of 4-phenoxybutyl bromide and 45.6 g (0.4 moles) of 1-formylpiperazine in 500 ml of 2-propanol was heated at reflux for 18 hours. The mixture was cooled and filtered. The filter was washed with 2-propanol and the filtrate was evaporated to a paste in vacuo. Water was added and the mixture was extracted three times with 200 ml portions of chloroform. The extracts were combined and evaporated to dryness. Then 250 ml of 5N sodium hydroxide was added to the residue. The mixture was refluxed for 18 hours with stirring, cooled and extracted twice with 250 ml portions of chloroform. The extracts were combined, dried over magnesium sulfate and evaporated to an oil. The oil was distilled bp 153°–156° C./0.05 mm of mercury and gave 33.4 g of 1-(4-phenoxybutyl)piperazine as a colorless liquid which crystallized on standing, mp 35°–36° C.

EXAMPLE 3

1-(2-Phenoxyethyl]piperazine

The procedure of Example 2 was repeated in entirety substituting 57.0 g (0.27 moles) of 2-bromoethyl phenyl ether for 4-phenoxybutyl bromide, using 61.6 g (0.54 moles) of 1-formylpiperazine in 300 ml of 2-propanol and refluxing the mixture for 8 hours. Evaporation of the final dried chloroform extracts gave 35 g of 1-[2-phenoxyethyl]piperazine as an oil.

EXAMPLE 4

1-[2,6-Dichlorophenyl)methyl]piperazine

A mixture of 95.9 g (0.49 moles) of 2,6-dichlorobenzyl chloride, 77.6 g (0.49 moles) of ethyl N-piperazinocarboxylate, 500 ml of isopropyl alcohol and 70 ml of 10N sodium hydroxide was heated at reflux for 18 hours. The solution was evaporated in vacuo and gave a crystalline residue. The residue in 100 ml of water was extracted twice with 200 ml portions of dichloromethane. The combined organic extract was dried over anhydrous sodium sulfate, filtered, evaporated in vacuo and gave an oil. The oil was subjected to Kugelrohr distillation, bp 117° C./0.45 mm of mercury and gave 136.4 g of 4-(2,6-dichlorobenzyl)-1-piperazinecarboxylic acid, ethyl ester as an oil.

A 136.4 g (0.43 mole) amount of the preceding product was refluxed with 141.7 ml of 12N hydrochloric acid for 4 hours. Then an additional 141.7 ml of 12N hydrochloric acid was added and the mixture was refluxed for an additional 24 hours.

The solution was cooled, 500 ml of water was added, and the mixture was made basic by the addition of 360 ml of 10N sodium hydroxide. The mixture was extracted with three 200 ml portions of dichloromethane. The combined extract was dried over anhydrous sodium sulfate and filtered. The filtrate was evaporated in vacuo and gave an oil. The oil was Kugelrohr distilled bp 115° C./0.7 mm of mercury and gave 63.6 g of material which crystallized on standing and gave white crystals mp 60°–65° C.

EXAMPLE 5

1-[3-Methoxyphenyl)methyl]piperazine

A mixture of 48.6 g (0.31 moles) of m-methoxybenzyl chloride, 49.0 g (0.31 moles) of ethyl N-piperazinocarboxylate, 250 ml of isopropyl alcohol and 35 ml of 10N sodium hydroxide was heated at reflux for 18 hours. The reaction mixture was evaporated in vacuo and gave an oil. The oil was Kugelrohr distilled bp 106° C./0.025 mm of mercury and gave 87.3 g of 4-[(3-methoxyphenyl)methyl]-1-piperazinecarboxylic acid, ethyl ether as an oil.

An 87.3 g (0.31 mole) amount of the preceding product was refluxed with 100 ml of 12N hydrochloric acid for 6 hours. Then an additional 50 ml of 12N hydrochloric acid was added and the mixture was refluxed for an additional 24 hours.

The reaction mixture was cooled, 350 ml of water was added, and the mixture was made basic by adding 240 ml of 10N sodium hydroxide.

The mixture was extracted with dichloromethane and treated as described in Example 4. Kugelrohr distillation bp 107° C./0.400 mm of mercury, gave 28.9 g of the desired product as an oil.

EXAMPLE 6

1-[(4-Methoxyphenyl)methyl]piperazine

A mixture of 248.3 g (1.59 moles) of 4-methoxybenzyl chloride, 250.8 g (1.59 moles) of ethyl N-piperazinocarboxylate, 1000 ml of isopropyl alcohol and 175 ml of 10N sodium hydroxide was heated at reflux for 18 hours. The reaction mixture was evaporated in vacuo and gave 429.2 g of an oil. A 121.7 g amount of the crude product was Kugelrohr distilled bp 93° C./0.075 mm of mercury and gave 94.5 g of purified 4-[(4-methoxyphenyl)methyl]-1-piperazinecarboxylic acid, ethyl ester as an oil.

A 377 g (1.35 mole) of the preceding product comprised of 307.5 g (1.10 moles) of crude product and 69.5 g (0.25 moles) of purified product was refluxed with 435 ml of 12N hydrochloric acid for 6 hours then was mixed with an equal volume of ice and allowed to stand for 16 hours in the cold. The mixture was made basic with 535 ml of 10N sodium hydroxide and extracted with 200 ml of diethyl ether. The aqueous layer was removed and the etheral layer was extracted with 100 ml of water. This bottom layer (aqueous) was mixed with sodium carbonate then extracted with 150 ml of dichlorothane. The dichloromethane extract was separated, dried over anhydrous sodium sulfate and filtered. The filtrate was evaporated in vacuo and gave an oil. The oil was Kugelrohr distilled bp 94° C./0.5 mm of mercury and gave 22.4 of the desired product as an oil.

EXAMPLE 7

1-[4-Chlorophenyl)methyl]piperazine

A mixture of 51.8 g (0.32 moles) of p-chlorobenzyl chloride, 50.8 g (0.32 moles) of ethyl N-piperazinocarboxylate, 250 ml of isopropyl alcohol and 35 ml of 10N sodium hydroxide was refluxed for 18 hours. The reaction mixture was evaporated in vacuo. The residue was mixed with water and extracted with dichloromethane. The organic layer was dried over anhydrous sodium sulfate, filtered, and evaporated in vacuo to a yellow liquid which crystallized and gave 238.5 g of solid.

A 236.9 g amount of the preceding solid was combined with 75 ml of 12N hydrochloric acid and refluxed for 24 hours. The reaction mixture was cooled, neutralized with sodium hydroxide and extracted with dichloromethane. The solvent was evaporated to an oil. The oil was Kugelrohr distilled, bp 102° C./0.15 mm of mercury and gave 47.7 g of the product of the Example as a liquid.

EXAMPLE 8

3-Amino-5-(4-benzyl-1-piperazinyl)-4-pyrazolecarbonitrile

A mixture of 4.25 g (0.025 moles) of [bis(methylthio)methylene]malonnitrile [K. A. Jensen and L. Henriksen, Acta Chem. Scand. 22 (4) 1107 (1968)] and 4.7 g (0.025 moles) of 1-benzylpiperazine in 100 ml of acetonitrile was stirred at reflux for 5 hours with evolution of methanethiol. Then 1.31 g (0.025 moles) of hydrazine hydrate was added and the solution was stirred at reflux for 16 hours, again with evolution of methanethiol. The reaction mixture was clarified while hot with activated charcoal and filtered through diatomaceous earth. The filtrate was cooled at −10° C. and a white precipitate developed. The precipitate was collected by filtration, washed with 50 ml of cold acetonitrile, air dried, then dried in vacuo at 60° C. and gave 4.5 g of crude product. The material was recrystallized from 150 ml of 2-propanol cooled at −10° C. and gave 2.8 g of the desired product as a white solid, mp 157°–158° C.

EXAMPLES 9–25

Additional examples of novel pyrazolylpiperazines which are listed in Table II were prepared in the manner described in Example 8, reacting equi-molar amounts of [bis(methylthio)methylene]malonnitrile with a piperazine derivative (hereinabove described, known in the literature or disclosed in our related Patent Application, Ser. No. 360,864) by refluxing for 2–20 hours in acetonitrile, giving a solution of the [4-substituted-1-piperazinyl)(methylthio)methylene]-propanedinitrile, which was refluxed with hydrazine hydrate in the solvent for 1–18 hours to obtain the pyrazolypiperazine products.

TABLE II

4-Substituted Pyrazolylpiperazines $$(CH_3S)_2C=C(CN)_2 + HN\diagup\diagdown N-R_3 \longrightarrow \left[(CN)_2C=\underset{\underset{CH_3S}{|}}{C}-N\diagup\diagdown N-R_3\right] \longrightarrow$$

$$\underset{H_2N}{\overset{H}{\underset{N}{\diagdown}}}\underset{CN}{\overset{N}{\diagup}}-N\diagup\diagdown N-R_3$$

| Ex. | Compound | $R_3$ | Description | MP °C. |
|---|---|---|---|---|
| 9 | 3-Amino-5-[4-[(3,4-dichlorophenyl)methyl]-1-piperazinyl]-1H—pyrazole-4-carbonitrile | —CH$_2$—C$_6$H$_3$Cl$_2$ (3,4-Cl$_2$) | White Solid | 176–178 |
| 10 | 3-Amino-5-[4-(3-phenylpropyl)-1-piperazinyl]-1H—pyrazole-4-carbonitrile, hydrochloride | —CH$_2$CH$_2$CH$_2$—C$_6$H$_5$ | White Solid | 143–145 (dec) |
| 11 | 3-Amino-5-[4-(2-furanylmethyl)-1-piperazinyl]-1H—pyrazole-4-carbonitrile | —CH$_2$-(2-furanyl) | White Solid | 138–140 |
| 12 | 5-Amino-3-[4-[(2-phenyl-2H—1,2,3-triazol-4-yl)methyl]-1-piperazinyl]-1H—pyrazole-4-carbonitrile | —CH$_2$-(2-phenyl-1,2,3-triazol-4-yl) | Colorless Crystals | 176–177 |
| 13 | 5-Amino-3-[4-(3-phenoxypropyl)-1-piperazinyl]-1H—pyrazole-4-carbonitrile | —CH$_2$CH$_2$CH$_2$—O—C$_6$H$_5$ | Cream Colored Crystals | 125–127 (dec) |

TABLE II-continued
4-Substituted Pyrazolylpiperazines $$(CH_3S)_2C=C(CN)_2 + HN\diagup\diagdown N-R_3 \longrightarrow \left[ \begin{array}{c} CH_3S \\ (CN)_2C=C-N\diagup\diagdown N-R_3 \end{array} \right] \longrightarrow$$

$$\begin{array}{c} H \\ N-N \\ H_2N \diagdown \diagup \diagdown N \diagup\diagdown N-R_3 \\ CN \end{array}$$

| Ex. | Compound | R₃ | Description | MP °C. |
|---|---|---|---|---|
| 14 | 5-Amino-3-[4-(4-phenoxybutyl)-1-piperazinyl]-1H—pyrazole-4-carbonitrile | —CH₂(CH₂)₂CH₂—O—C₆H₅ | Cream Colored Crystals | 109–112 |
| 15 | 5-Amino-3-[4-(2-phenoxyethyl)-1-piperazinyl]-1H—pyrazole-4-carbonitrile | —CH₂CH₂—O—C₆H₅ | Off-white Crystals | 147–149 (dec) |
| 16 | 3-Amino-5-[4-(3-phenyl-2-propenyl)-1-piperazinyl]-1H—pyrazole-4-carbonitrile | —CH₂CH=CH—C₆H₅ | White Solid | 216–218 |
| 17 | 3-Amino-5-(4-methyl-1-piperazinyl)-1H—pyrazole-4-carbonitrile | —CH₃ | White Solid | 205–208 |
| 18 | 3-Amino-5-(4-phenyl-1-piperazinyl)-1H—pyrazole-4-carbonitrile | —C₆H₅ | White Solid | 166–168 |
| 19 | 3-Amino-5-[4-(2-pyridinyl)-1-piperazinyl]-1H—pyrazole-4-carbonitrile | 2-pyridinyl | White Solid | 180–182 |
| 20 | 3-Amino-5-[4-(2-hydroxyethyl)-1-piperazinyl]-1H—pyrazole-4-carbonitrile | —CH₂CH₂—OH | White Solid | 174–176 |
| 21 | 3-Amino-5-[4-[(3-chlorophenyl)methyl]-1-piperazinyl)]-1H—pyrazole-4-carbonitrile | —CH₂—(3-ClC₆H₄) | White Crystals | 162–165 |
| 22 | 3-Amino-5-[4-[(2,6-dichlorophenyl)methyl]-1-piperazinyl]-1H—pyrazole-4-carbonitrile | —CH₂—(2,6-Cl₂C₆H₃) | White Crystals | 206–212 |
| 23 | 3-Amino-5-[4-[(4-methoxyphenyl)methyl]-1-piperazinyl]-1H—pyrazole-4-carbonitrile | —CH₂—(4-CH₃OC₆H₄) | White Crystals | 223–228 |
| 24 | 3-Amino-5-[4-[(3-methoxyphenyl)methyl]-1-piperazinyl]-1H—pyrazole-4-carbonitrile | —CH₂—(3-CH₃OC₆H₄) | White Crystals | 185–188 |

TABLE II-continued

4-Substituted Pyrazolylpiperazines

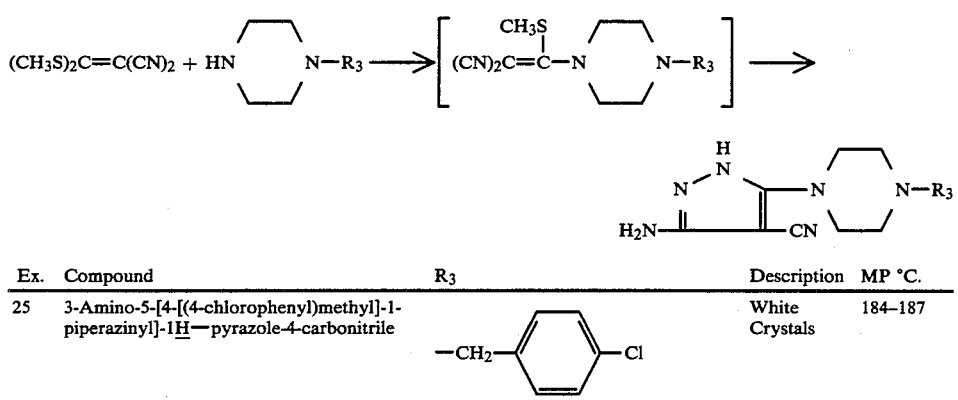

| Ex. | Compound | R₃ | Description | MP °C. |
|---|---|---|---|---|
| 25 | 3-Amino-5-[4-[(4-chlorophenyl)methyl]-1-piperazinyl]-1H—pyrazole-4-carbonitrile | —CH₂—C₆H₄—Cl | White Crystals | 184–187 |

EXAMPLE 26

3-Amino-5-(4-benzyl-1-piperazinyl)-4-pyrazolecarboxamide

A 4.0 g (0.0142 mole) amount of 3-amino-5-(4-benzyl-1-piperazinyl)-4-pyrazolecarbonitrile (prepared as described in Example 8) was dissolved in 15 ml of concentrated sulfuric acid by stirring. The solution was heated on a steam bath for 4 hours, then allowed to stand at room temperature for 16 hours. The solution was poured into 400 ml of ice/water and made basic with 50 ml of concentrated ammonium hydroxide. The mixture was cooled at 5° C. for one hour. Then the precipitate was collected by filtration, washed with water and air dried.

The precipitate was dissolved in 100 ml of hot ethanol then 100 ml of water was added at the boil. The solution was clarified hot with activated charcoal and filtered through diatomaceous earth. The solution was cooled and 100 ml of water was added. Then the solution was evaporated in vacuo until turbidity developed. The mixture was cooled at 5° C. and the precipitate formed was collected, washed with water and air dried. The solid was recrystallized again from ethanol and water as above, then was dried in vacuo at 60° C. and gave 1.0 g of the desired product as a white solid, mp 234°–236° C.

EXAMPLE 27

N-[4-Cyano-5-[4-(phenylmethyl)-1-piperazinyl]-1H-pyrazol-3-yl)acetamide

A 2.82 g (0.01 mole) amount of 3-amino-5-(4-benzyl-1-piperazinyl)-4-pyrazolecarbonitrile (prepared as described in Example 8) was added to 50 ml of acetic anhydride with stirring. After nearly complete solution a heavy precipitate was formed. The mixture was stirred for 18 hours at room temperature beneath a drying tube containing a desicant.

The precipitate was collected by filtration, washed with 50 ml of ether, then with 100 ml of saturated sodium bicarbonate (with trituration), then with 50 ml of water. The material was air dried, then dried in vacuo at 60° C. The solid was recrystallized from 200 ml of boiling ethanol after clarification with activated charcoal and filtration, by cooling at −10° C. The precipitate was collected, washed with 25 ml of cold ethanol, then 50 ml of ether. The solid was air dried, then dried in vacuo at 60° C. and gave 1.6 g of the product of the Example as a white solid, mp 203°–204° C.

EXAMPLE 28

N-[4-Cyano-5-[4-(4-phenylmethyl)-1-piperazinyl]-1H-pyrazol-3-yl]methanesulfonamide A 4.2 g (0.015 mole) amount of 3-amino-5-(4-benzyl-1-piperazinyl)-4-pyrazolecarbonitrile (prepared as described in Example 8) was dissolved in 100 ml of pyridine. The solution was cooled to 0° C. and stirred as 1.6 ml of methanesulfonyl chloride was added. The mixture was stirred at 0°–5° C. for one hour, then at room temperature for 16 hours. The reaction mixture was taken to dryness in vacuo. The residue was shaken with 100 ml of water. The mixture was then adjusted to pH 8.0 with a solution of saturated sodium bicarbonate and allowed to stand at room temperature.

The precipitate was collected and air dried, then was recrystallized twice from ethanol, clarified hot with activated charcoal and cooled at −10° C. each time. The final product was collected, air dried and dried in vacuo at 100° C. and gave 1.3 g of the product of the Example as a white solid, mp 176°–177° C.

We claim:

1. A compound selected from the group consisting of those of the formula:

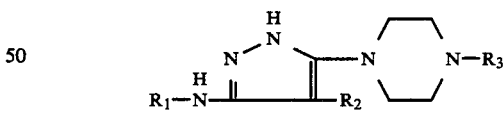

wherein R₁ is hydrogen, alkyl(C₁–C₃)carbonyl or alkyl(C₁–C₃)sulfonyl; R₂ is cyano or carbamoyl; and R₃ is methyl, benzyl, 3-phenylpropyl, 3-phenyl-2-propenyl, β-hydroxyethyl, 3-chlorobenzyl, 4-chlorobenzyl, 3,4-dichlorobenzyl, 2,6-dichlorobenzyl, 2-phenoxyethyl, 3-phenoxypropyl, 4-phenoxybutyl, 3-methoxybenzyl, 4-methoxybenzyl, 2-furanylmethyl, 2-pyridyl or (2-phenyl-2H-1,2,3-triazol-4-yl)methyl; and the pharmacologically acceptable acid-addition salts thereof.

2. The compound in accordance with claim 1; 3-amino-5-(4-benzyl-1-piperazinyl)-4-pyrazolecarbonitrile.

3. The compound in accordance with claim 1; 3-amino-5-(4-benzyl-1-piperazinyl)-4-pyrazolecarboxamide.

4. The compound in accordance with claim 1; 3-amino-5-[4-[(3,4-dichlorophenyl)methyl]-1-piperazinyl]-1H-pyrazole-4-carbonitrile.

5. The compound in accordance with claim 1; 3-amino-5-[4-(3-phenylpropyl)-1-piperazinyl]-1H-pyrazole-4-carbonitrile, hydrochloride.

6. The compound in accordance with claim 1; 3-amino-5-[-4-2-furanylmethyl-1-piperazinyl]-1H-pyrazole-4-carbonitrile.

7. The compound in accordance with claim 1; 5-amino-3-[4-[(2-phenyl-2H-1,2,3-triazol-4-yl)-methyl]-1-piperazinyl]-1H-pyrazole-4-carbonitrile.

8. The compound in accordance with claim 1; 5-amino-3-[4-(3-phenoxypropyl)-1-piperazinyl]-1H-pyrazole-4-carbonitrile.

9. The compound in accordance with claim 1; 5-amino-3-[4-(4-phenoxybutyl)-1-piperazinyl]-1H-pyrazole-4-carbonitrile.

10. The compound in accordance with claim 1; 5-amino-3-[4-(2-phenoxyethyl)-1-piperazinyl]-1H-pyrazole-4-carbonitrile.

11. The compound in accordance with claim 1; 3-amino-5-[4-(3-phenyl-2-propenyl)-1-piperazinyl]-1H-pyrazole-4-carbonitrile.

12. The compound in accordance with claim 1; N-[4-cyano-5-[4-(phenylmethyl)-1-piperazinyl]-1H-pyrazol-3-yl].

13. The compound in accordance with claim 1, 3-amino-5-(4-methyl-1-piperazinyl)-1H-pyrazole-4-carbonitrile.

14. The compound in accordance with claim 1; 3-amino-5-[4-[(3-chlorophenyl)methyl]-1-piperazinyl]-1H-pyrazole-4-carbonitrile.

15. The compound in accordance with claim 1; 3-amino-5-[4-[(4-methoxyphenyl)methyl]-1-piperazinyl]-1H-pyrazole-4-carbonitrile.

16. The compound in accordance with claim 1; 3-amino-5-[4-[(3-methoxyphenyl)methyl]-1-piperazinyl]-1H-pyrazole-4-carbonitrile.

17. The compound in accordance with claim 1; 3-amino-5-[4-[(4-chlorophenyl)methyl]-1-piperazinyl]-1H-pyrazole-4-carbonitrile.

18. The method of treating hypertension in a mammal which comprises administering to said mammal an effective antihypertensive amount of a compound of claim 1.

19. A hypotensive composition of matter in dosage unit form comprising from about 50 mg to about 150 mg per dosage unit of a compound of claim 1 in association with a pharmaceutical carrier.

* * * * *